United States Patent [19]

Plöger

[11] 4,122,151
[45] Oct. 24, 1978

[54] PROCESS OF STABILIZATION OF DIBASIC CALCIUM PHOSPHATE DIHYDRATE AGAINST HYDROLYSIS WITH CYCLIC AMINOPHOSPHONIC ACIDS

[75] Inventor: Walter Plöger, Hilden, Germany

[73] Assignee: Henkel Kommanditgesellschaft auf Aktien, Dusseldorf, Germany

[21] Appl. No.: 636,731

[22] Filed: Dec. 1, 1975

[30] Foreign Application Priority Data

Nov. 30, 1974 [DE] Fed. Rep. of Germany ....... 2456787

[51] Int. Cl.² .................. C01B 15/16; C01B 25/26
[52] U.S. Cl. ............................ 423/265; 423/308; 423/311; 424/57
[58] Field of Search ................ 423/299–323, 423/265, 268; 424/49, 52, 57, 128

[56] References Cited

U.S. PATENT DOCUMENTS

| | | | |
|---|---|---|---|
| 2,018,410 | 10/1935 | McDonald et al. | 424/57 |
| 2,876,166 | 3/1959 | Nebergall | 424/52 |
| 3,012,852 | 12/1961 | Nelson | 23/109 |
| 3,066,056 | 11/1962 | Schlaeger et al. | 23/108 |
| 3,169,096 | 2/1965 | Schlaeger et al. | 424/57 |
| 3,244,478 | 4/1966 | Stahlheber | 423/311 |
| 3,308,029 | 3/1967 | Saunders et al. | 424/52 |
| 3,442,604 | 5/1969 | Smith et al. | 23/108 |
| 3,488,419 | 1/1970 | McCune et al. | 424/49 |
| 3,678,154 | 7/1972 | Widder et al. | 424/52 |
| 3,792,152 | 2/1974 | Kim | 423/311 |
| 3,925,456 | 12/1975 | Ploger et al. | 424/54 X |

Primary Examiner—O. R. Vertiz
Assistant Examiner—Gregory A. Heller
Attorney, Agent, or Firm—Hammond & Littell

[57] ABSTRACT

A process for stabilizing dibasic calcium phosphate dihydrate against hydrolysis comprising treating an aqueous suspension of dibasic calcium phosphate dihydrate at a pH of from 5 to 10 with a cyclic aminophosphonic acid of the formula

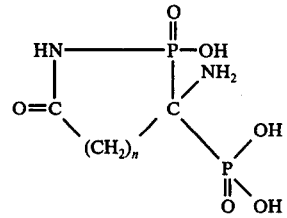

wherein n is an integer from 1 to 3, or a water-soluble salt thereof, in an amount of from 0.01 to 5% by weight with reference to the dibasic calcium phosphate dihydrate; as well as tooth cleaning preparations containing the stabilized dibasic calcium phosphate dihydrate.

5 Claims, No Drawings

PROCESS OF STABILIZATION OF DIBASIC CALCIUM PHOSPHATE DIHYDRATE AGAINST HYDROLYSIS WITH CYCLIC AMINOPHOSPHONIC ACIDS

RELATED ART

Dibasic calcium phosphate dihydrate having the formula $CaHPO_4 \cdot 2H_2O$ is a polishing substance frequently utilized in tooth cleaning preparations as, for example, toothpastes and powders. For this purpose it may be used alone or in admixture with other polishing substances as, for example, silica gel or plastics cleaning substances. Besides having some properties advantageous for this purpose, however, the calcium-hydrogenphosphate-dihydrate has the disadvantage that it is not stable to aqueous hydrolysis. This lack of stability to hydrolysis has a particularly aggravating effect in preparations containing water as, for example, toothpastes. However, also in products such as tooth powders it may lead to undesired results. In the presence of moisture, dibasic calcium phosphate dihydrate hydrolyzes easily with liberation of acid, in which case basic phosphates are formed, which mostly have an apatite structure. The processes which thereby take place may be theoretically represented by the following empirical reaction:

$$5CaHPO_4 + H_2O \rightarrow Ca_5(OH)(PO_4)_3 + 2H_3PO_4$$

In this reaction the dihydrate water of crystallization has been disregarded. The speed as well as the end point of this reaction is influenced by several circumstances such as temperature, pH of the mixture and its composition. The temperature has a particularly great influence, since the dibasic calcium phosphate dihydrate decomposes at temperatures as low as from 36° C. with formation of anhydrous dibasic calcium phosphate, hydroxyapatite, phosphoric acid and water, or respectively, some calcium phosphate solution. Consequently, the possibility results that even toothcleaning preparations produced without addition of water can hydrolyze. Temperatures of 36° C. and over, moreover, may easily occur in the making of the preparations containing dibasic calcium phosphate dihydrate or, for example, in the storage of finished products, especially in tropical zones.

The acid liberated in the hydrolysis not only, in some cases, alters the pH value of the mixture, but it may change the whole structure of the product; for example, it may cause a paste to solidify; powders may stick together or agglomerate, and tablets may disintegrate. If, in addition to the dibasic calcium phosphate dihydrate, carbonates are present in the mixture, as may be the case with tooth cleaning preparations, during the hydrolysis evolution of carbon dioxide occurs as a very unpleasant side phenomenon, which in some cases may lead to bursting of the container, as for example, tubes, or at least to an expansion or bulge.

For the use of a polishing agent as cleaning material in toothcleaning preparations, its abrasive behavior is of decisive importance, since products to be used for this purpose must only have an abrasive power which does not cause damage to the teeth. Owing to its favorable abrasive behavior, dibasic calcium phosphate dihydrate already enjoys great popularity as a cleaning material in tooth cleaning preparations. If, however, a conversion into the substantially harder apatite is caused by the hydrolysis, in some circumstances abrasive agents or agents with uncontrolled abrasive power may be formed.

Therefore, earlier attempts have already been made to stabilize dibasic calcium phosphate dihydrate against hydrolysis, in order to make possible its use in tooth cleaning agents without any problems. For this purpose various compounds such as pyrophosphoric acid, sodium/calcium pyrophosphate or sodium pyrophosphate have been added to a suspension of dibasic calcium phosphate dihydrate in water; the suspension was then filtered and the product obtained was incorporated in the tooth cleaning preparations. All these stabilizing compounds were not satisfactory, however, since in some cases complicated further treatments of the products were necessary in order to obtain a sufficient stability, and in other cases the process itself caused considerable technical difficulties.

It has further been proposed to use specific phosphonic acids, such as 1-hydroxyethane-1,1-diphosphonic acid or amino-tris-(methylenephosphonic acid) as stabilizers against hydrolysis of dibasic calcium phosphate dihydrate. These phosphonic acids as well as other phosphonic acids mentioned in this connection, however, have two essential disadvantages in respect to the stabilization of dibasic calcium phosphate dihydrate. Their stabilizing action still leaves much to be desired and the stabilization raises technical problems. Only products with the greatest possible long lasting inhibiting action are suitable for the use as stabilizer of dibasic calcium phosphate dihydrate for tooth cleaning preparations, since the inhibiting action of the phosphonic acids only lasts a certain time, and then usually stops suddenly. In the case of the already proposed phosphonic acids, the inhibiting action is not particularly great and does not last sufficiently long. Further, there is the disadvantage that the inhibiting action of the said phosphonic acids does not increase in every case with the increase of the amount added, but on the contrary falls off again, owing to which the desired dosing is technically difficult to carry out.

OBJECTS OF THE INVENTION

An object of the present invention is the development of a process for stabilizing dibasic calcium phosphate dihydrate against hydrolysis consisting essentially of suspending dibasic calcium phosphate dihydrate in an aqueous medium at a pH of from 5 to 10, containing from 0.01 to 5% by weight based on the content of said dibasic calcium phosphate dihydrate of a cyclic aminophosphonic compound selected from the group consisting of (A) compounds of the formula

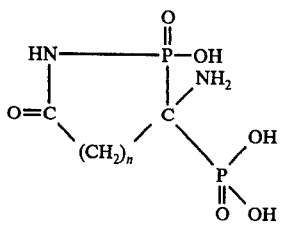

wherein $n$ is an integer from 1 to 3, and (B) water-soluble salts thereof, and separating said stabilized dibasic calcium phosphate dihydrate.

Another object of the present invention is the obtaining of a stabilized dibasic calcium phosphate dihydrate.

A further object of the present invention is the obtaining of tooth cleaning preparations containing a stabilized dibasic calcium phosphate dihydrate.

These and other objects of the present invention will become more apparent as the description thereof proceeds.

DESCRIPTION OF THE INVENTION

It has now been found that a satisfactory and easily effected stabilization of dibasic calcium phosphate dihydrate against hydrolysis is possible by treating the dibasic calcium phosphate dihydrate in aqueous medium at a pH of from 5 to 10, preferably from 6 to 8, with a cyclic aminophosphonic acid of the general formula

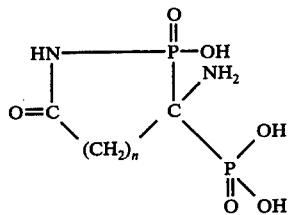

in which $n$ is an interger of from 1 to 3, or a water-soluble salt thereof, in an amount of from 0.01 to 5% by weight, preferably from 0.03 to 2% by weight, referred to the amount of dibasic calcium phosphate dihydrate employed.

More particularly, the invention relates to a process for stabilizing dibasic calcium phosphate dihydrate against hydrolysis consisting essentially of suspending dibasic calcium phosphate dihydrate in an aqueous medium at a pH of from 5 to 10, containing from 0.01 to 5% by weight based on the content of said dibasic calcium phosphate dihydrate of a cyclic aminophosphonic compound selected from the group consisting of (A) compounds of the formula

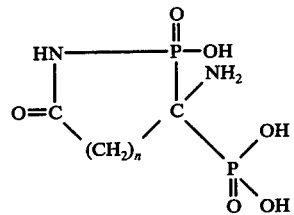

wherein $n$ is an integer from 1 to 3, and (B) water-soluble salts thereof, and separating said stabilized dibasic calcium phosphate dihydrate, as well as the stabilized dibasic calcium phosphate dihydrate so produced and tooth cleaning preparations containing the same.

In carrying out the process of the invention, the cyclic aminophosphonic acid or its water-soluble salt, the dibasic calcium phosphate dihydrate and water may be admixed in any manner. For example, the cyclic aminophosphonic acid or its water-soluble salt may be used in the mixture either as an aqueous solution or in solid form and the dibasic calcium phosphate dihydrate may be used in the mixture either as an aqueous suspension or in solid form.

The preparation of the aminophosphonic acids to be used according to the present invention, or their water-soluble salts may be carried out in a simple way by reacting dicarboxylic acid derivatives of the formula $$X - (CH_2)_n - X$$

in which $n$ represents an integer of from 1 to 3 and X represents a nitrile group or $-CONH_2$, with phosphorus trihalides or mixtures of phosphorus trihalides and phosphorous acid, hydrolyzing the reaction product and if desired converting into the salts, as are described in copending commonly-assigned U.S. patent application Ser. No. 498,996, filed Aug. 20, 1974, now U.S. Pat. No. 3,925,456.

The reaction may be carried out, for example, by first melting the dicarboxylic acid diamide with phosphorous acid and slowly adding $PCl_3$ with stirring. The mostly viscous reaction product formed is then hydrolyzed by addition of water. An addition of an acid is not necessary, since the reaction product itself has an acid reaction. Starting from dicarboxylic acid dinitrile, however, this may also be dissolved in an inert solvent as, for example, dioxane or chlorinated hydrocarbons, and then treated with phosphorus trihalide. After that, phosphorous acid is then added and after addition of water, the solution is hydrolyzed. In the last-named process the phosphorous acid may also be omitted, if desired. Suitable phosphorus trihalides are especially phosphorus trichloride and phosphorus tribromide. The latter has been found particularly suitable when nitriles are used as the reaction partner. The molar proportions of dicarboxylic acid derivative and phosphorus compound are 1:2 to 1:6, preferably 1:4. The above-mentioned dicarboxylic acid derivatives used are those of malonic acid ($n=1$), succinic acid ($n=2$) and glutaric acid ($n=3$).

Advantageously the cyclic aminophosphonic acids may also be employed in the form of their water-soluble salts such as their alkali metal salts, especially lithium, sodium and potassium salts, and their ammonium salts. The conversion into the salts may easily be carried out by partial or complete neutralization with the corresponding bases.

The stabilization according to the present invention may either be carried out before isolation of the dibasic calcium phosphate dihydrate from the reaction medium in which it is prepared or in a later separate treatment process. The preparation of the dibasic calcium phosphate dihydrate may be effected according to processes known from the literature, for example, from calcium hydroxide and phosphoric acid.

If the stabilization is to be carried out on previously isolated dibasic calcium phosphate dihydrate which is the preferred method of production, this previously isolated dibasic calcium phosphate dihydrate is treated with an aqueous solution of the stabilizer, the pH of the solution being adjusted to from 5 to 10, preferably from 6 to 8. However, even if the stabilization is effected before isolation of the dibasic calcium phosphate dihydrate from the reaction medium, the aqueous suspension is set at a pH of 5 to 10, preferably 6 to 8, with the addition of the stabilizer. The amount of stabilizer required can easily be found by testing. It has been found that in general 0.01 to 5% by weight, preferably 0.03 to 2% by weight, based on the amount of dibasic calcium phosphate dihydrate to be stabilized is sufficient in the event no other stabilizers are present. The amount, within the indicated limits is dependent on (a) the extent of the desired stabilization, (b) the particle size, surface and surface structure of the dibasic calcium phosphate dihydrate prepared, and (c) the time of contact between the stabilizer and the product to be stabilized. It has further been found suitable to use the water-soluble salts of the cyclic aminophosphonic acids, as for example, alkali metal salts, especially sodium salts. If the free acids are to be used, it may be necessary to correct for pH deviations, for example, by addition of calcium hydroxide or calcium oxide. Owing to the small amounts of the added cyclic aminophosphonic acid, however, this is often unnecessary. The stabilizers to be used according to the present invention may also be used in combination with other substances, such as other stabilizers, aids to precipitation or protective colloids as, for example, with pyrophosphates, tripolyphosphates and other polymeric phosphates, polysilicates, polycarboxylates, lignin derivatives, gums and polysaccharides.

Cyclic aminophosphonic acids of the above-mentioned general formula which are also substituted on the nitrogen atom also show a stabilizing action, but this is substantially less and, therefore, of little technical interest.

The present invention relates primarily to the preparation of a dibasic calcium phosphate dihydrate stabilized aginst hydrolysis, for use in tooth cleaning preparations. Such stabilized products, however, may also be advantageous in other fields of application. The tooth cleaning preparations to be prepared according to the present invention may contain, in addition to the stabilized dibasic calcium phosphate dihydrate serving as polishing material, the usual constituents such as, for example, thickeners, surface-active compounds or tensides, emulsifiers, bactericides, and flavoring substances. A toothpaste is the preferred form of the tooth cleaning preparations with a content of stabilized dibasic calcium phosphate dihydrate according to the present invention.

Toothpastes are generally pasty preparations based on water, which contain thickeners, wetting and foaming agents, moisture-retention agents, polishing, scouring or cleaning substances, aroma-imparting substances, taste correctors, antiseptic and other substances valuable as mouth cosmetics. The content of polishing substances in the toothpastes, i.e., the content of the dibasic calcium phosphate dihydrate which is to be used according to the present invention and which is stabilized against hydrolysis, will generally vary from 25 to 60% by weight, referred to the total mass of the toothpaste. The wetting and foaming agents employed are especially soap-free anionic surface-active compounds such as fatty alcohol sulfates, for example, sodium lauryl sulfate, monoglyceride sulfates, sodium lauryl sulfoacetate, sarcosides, taurides and other anionic surface-active compounds which do not affect the taste, in amounts from 0.5 to 5% by weight. For the preparation of the binder for toothpaste, all thickeners usual for this purpose may be used, such as hydroxyethylcellulose, sodium carboxymethylcellulose, tragacanth, carragean moss, agar-agar and gum arabic, as well as additionally finely divided silicic acids, all in amounts of from 0.1 to 5% by weight of the whole toothpaste. As moisture-retention means, glycerine and sorbitol are of principal importance, in amounts which may be up to one-third or from 5 to 33⅓% by weight of the whole toothpaste. Water is also present in amounts of from 10 to 50% by weight of the whole toothpaste. With toothpowders, the water, thickeners and moisture-retention means are omitted. The desired aroma and taste requirements can be attained by an addition of essential oils such as peppermint, clove, wintergreen and sassafras oils, as well as by sweetening agents, such as saccharin, dulcin, dextrose or laevulose.

In addition, fluorine-containing compounds serving for the control of caries or for caries prophylaxis may be present. These are present in amounts of from 0 to 2% measured as fluorine ions of the whole tooth cleaning preparations. Such fluorine-containing compounds are, for example, sodium fluoride, potassium fluoride, aluminum fluoride, monoethanolamine-hydrofluoride, hexadecylaminehydrofluoride, oleylamine-hydrofluoride, N,N',N'-tri-(polyoxyethylene)-n-hexadecyl-propylenediamine-dihydrofluoride, bis-(hydroxyethyl)-amino-propyl-N-hydroxyethyl-octadecylamine-dihydrofluoride, magnesium aspartate-hydrofluoride, and tin fluoride. Also fluorine compounds in which the fluorine is present primarily in a preponderantly non-ionic bond, which, however, may split off fluoride, for example, by hydrolysis or other chemical reactions, such as sodium monofluorophosphate, potassium monofluorophosphate, magnesium monofluorophosphate, indium fluorozirconate, zirconium hexafluorogermanate, etc.

Optionally, further cleaning and filling substances possibly also used in the tooth cleaning preparations are present, as for example, plastics particles, silica gels or pyrogenic silicic acids.

The preparation of the dibasic calcium phosphate dihydrate stabilized against hydrolysis is generally effected by treatment of a previously isolated dibasic calcium phosphate dihydrate with an aqueous solution of the stabilizer. It is, of course, also possible to stabilize a dibasic calcium phosphate dihydrate present in an already finished toothpaste subsequently against the reaction with fluorine ions by an addition thereto of salts of the cyclic aminophosphonic acids. Such measures may be employed in special circumstances, but should remain confined to exceptions, since the result of such a difficultly controllable treatment in such a heterogeneous system as that of a toothpaste, is not always fully ensured.

The following examples illustrate further the present invention without, however, being restricted thereto.

EXAMPLES

First the preparation of some cyclic aminophosphonic acids to be used as stabilizers according to the present invention are described.

STABILIZER A

Preparation of 2-hydroxy-2-oxo-3-amino-3-phosphonyl-5-oxo-1,2-azaphosphacyclopentane, $n=1$

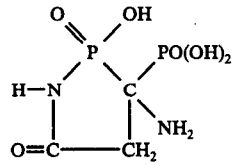

102 gm of malonic acid diamide (1.0 mol) and 164 gm of $H_3PO_3$ (2.0 mols) were melted at 70° C. with exclusion of moisture and 175 ml of $PCl_3$ (2.0 mols) were slowly added while stirring. A viscous yellow mass was formed which after standing for four hours was hydrolyzed with 1 liter of $H_2O$. After addition of activated charcoal and filtering, the filtrate was concentrated to 400 ml and precipitation was effected with 4 liters of ethanol to give a white crystalline substance. The substance was dried at 50° C. in a vacuum drying cabinet. The crude yield was 142 gm, or about 53% of theory.

The compound was first isolated as dihydrate, which by the titrimetric method had a molecular weight of 266 (calculated 266.1).

After more rigorous drying the water-free compound was obtained with a molecular wieght of 228 (calculated 230).

In the infra-red spectrum the substance showed a $\gamma_{CO}$ band at 1670 cm$^{-1}$ and a $\delta_{NH}$ band at 1615 cm$^{-1}$. It melted at 180° C. with decomposition.

STABILIZER B

Preparation of 2-hydroxy-2-oxo-3-amino-3-phosphonyl-6-oxo-1,2-azaphosphacyclohexane, $n=2$

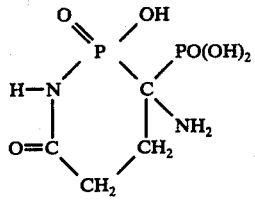

232 gm of succinic acid diamine (2.0 mols) and 328 gm of $H_3PO_3$ (4.0 mols) were melted at 70° C. with exclusion of moisture and 350 ml of $PCl_3$ (4.0 mols) were slowly added thereto under stirring. After 4 hours the viscous yellow mass formed was hydrolyzed with 2 liters of $H_2O$. The solution was treated with activated charcoal and filtered. The filtrate was concentrated to 500 ml and precipitation was effected with 3 liters of ethanol and 3 liters of acetone to give a white crystalline substance. Crude yield 180 gm, about 35% of theory.

The compound was first obtained as the monohydrate, and the titrimetrically determined molecular weight was 260 (calculated 262.1).

After drying at 80° C. in vacuo the anhydrous cyclic compound was obtained with a molecular weight of 244 (calculated 244). The infra-red spectrum showed a very broad $\gamma_{CO}$ band at 1640 cm$^{-1}$, by which the $\delta_{NH}$ band was masked. It melted at 320° C. with decomposition.

STABILIZER C

Preparation of 2-hydroxy-2-oxo-3-amino-3-phosphonyl-7-oxo-1,2-azaphosphacycloheptane, $n=3$

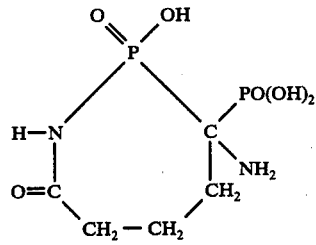

55 gm of glutaric acid diamide (0.42 mol) and 140 gm of $H_3PO_3$ (1.7 mols) were melted at 70° C. and then 149 ml of $PCl_3$ (1.7 mols) were slowly added thereto. After a further 4 hours at 80° C., the mixture was hydrolyzed with 400 ml of $H_2O$ and the hot solution was treated with activated charcoal and filtered. The white cyclic diphosphonic acid was precipitated from the filtrate with ethanol and acetone. Crude yield 40 gm, about 35% of theory.

After drying a short time at 50° C. the substance was obtained as monohydrate. The molecular weight was determined titrimetrically as 276 (calculated 276). After drying at 80° C. in vacuo the anhydrous substance was obtained with a molecular weight of 260 (calculated 258). The product melted at 285° C. with decomposition. In the infra-red spectrum, the $\gamma_{CO}$ band was at 1660 cm$^{-1}$ and the $\delta_{NH}$ band was at 1615 cm$^{-1}$.

The following examples serve to demonstrate the superior stabilizing activity of the cyclic aminophosphonic acids to be used as stabilizers according to the present invention. In these examples, the products stabilized according to the present invention were not only compared with untreated dibasic calcium phosphate dihydrate but also compared with products which were obtained by treatment with other structurally different phosphonic acids.

As a measure of the stabilizing action, the hydrolysis of the dibasic calcium phosphate dihydrate in an aqueous suspension was followed at 60° C. The acid formed during the hydrolysis was continuously back-titrated with alkali, owing to which a constant pH value of the hydrolysis solution was ensured during the whole hydrolysis. The consumption of alkali was continuously followed over the entire period and consequently gave at each point of time a measure for the progress of the hydrolysis. The consumption of alkali may also be given in percentages of the final consumption, which then corresponds to the percentage rate of phosphate which is hydrolyzed at the respective point of time. The titration over the given time can advantageously be carried out by means of a recording autotitrator, which is arranged for pH-stat measurements.

In order to be able to compare truly the individual experiments, it is not only necessary during the measurements to keep constant, for example, the parameters of temperature, pH, amount of dibasic calcium phosphate dihydrate and amount of solution, but also the same dibasic calcium phosphate dihydrate must always be used.

This requirement was fulfilled in the present case in that, according to the directions of Jensen and Rathlev (Bailor's "Inorganic Synthesis," Vol. 4, New York-Toronto-London 1953, pp. 1/218, 20), a large quantity of well crystallized dibasic calcium phosphate dihydrate was prepared and the fraction of particle size between 0.5 and 1 mm was sieved out and employed in the following.

EXAMPLE 1

15 mg of 2-hydroxy-2-oxo-3-amino-3-phosphonyl-7-oxo-1,2-azaphosphacycloheptane (0.15%, based on the $CaHPO_4 \cdot 2H_2O$ employed) were dissolved in 10 ml of water. The solution was adjusted with NaOH to pH 7.5 and made up to 25 ml with water. 15 ml of barbital buffer of pH 7.5 were added thereto. Then 10 gm of dibasic calcium phosphate dihydrate were suspended in this solution, left for 24 hours in the solution, then filtered off by suction, washed with a little water and alcohol and dried.

In the same way dibasic calcium phosphate dihydrate was prepared which had been treated respectively with 37 mg (0.37%, based on the $CaHPO_4 \cdot 2H_2O$) of the following phosphonic acids:

1-hydroxyethane-1,1-diphosphonic acid
N-methylaminomethanediphosphonic acid
2-phosphonopropane-1,2-dicarboxylic acid
dimethylaminomethanediphosphonic acid.

A similar sample was also made without addition of phosphonic acid.

2.58 gm of each of these treated dibasic calcium phosphate dihydrates were mixed in a temperature controlled vessel with 3 ml of a barbital buffer solution of pH 7.6 and 7 ml of water. To this was added a mixture heated to about 80° C. of 7 ml of barbital buffer pH 8 and 33 ml of water. A $CaHPO_4.2H_2O$ suspension at 60° C. and a pH of 7.5 was obtained. The pH of the suspension was kept constant by means of an automatic titrator by addition of NaOH and the consumption of alkaline liquor caused by the hydrolysis was recorded over the entire hydrolysis period.

The following times of hydrolysis resulted for the individual samples, which are shown in the following Table 1.

TABLE 1

| Inhibitor | | Time for x % Hydrolysis (Minutes) | | | | | |
|---|---|---|---|---|---|---|---|
| | | 10% | 20% | 40% | 60% | 80% | 100% |
| Without addition | | 7.5 | 7.8 | 8.0 | 8.2 | 8.3 | 9.4 |
| 0.15% | 2-hydroxy-2-oxo-3-amino-3-phosphonyl-7-oxo-1,2-azaphosphacycloheptane | 210 | 210 | 300 | 305 | 315 | 330 |
| 0.37% | 1-hydroxyethane-1,1-diphosphonic acid | 30 | 32 | 35 | 39 | 42 | 52 |
| 0.37% | 2-phosphonopropane-1,2-dicarboxylic acid | 7 | 8 | 11 | 16 | 24 | 35 |
| 0.37% | N-methylaminomethane-diphosphonic acid | 65 | 68 | 71 | 73 | 74 | 80 |

TABLE 1-continued

| Inhibitor | | Time for x % Hydrolysis (Minutes) | | | | | |
|---|---|---|---|---|---|---|---|
| | | 10% | 20% | 40% | 60% | 80% | 100% |
| Without addition | | 7.5 | 7.8 | 8.0 | 8.2 | 8.3 | 9.4 |
| 0.37% | N,N-dimethyl-amino-methane-diphosphonic acid | 19 | 21 | 23 | 26 | 31 | 43 |

Although less than half the quantity of acid according to the present invention was used compared with the other phosphonic acids, the results show that a considerably better stabilization against hydrolysis could already be obtained therewith.

EXAMPLE 2

As in Example 1 samples of dibasic calcium phosphate dihydrate were prepared, which had been treated with the amounts of the respective inhibitors indicated in Table 2. Hydrolysis was effected and measured as in Example 1. The measured times of hydrolysis are given in the following Table 2.

TABLE 2

| | Inhibitor | Time for x % Hydrolysis (Minutes) | | | | | |
|---|---|---|---|---|---|---|---|
| | | 10% | 20% | 40% | 60% | 80% | 100% |
| 0.15% | 2-hydroxy-2-oxo-3-amino-3-phosphonyl-7-oxo-1,2-azaphosphacycloheptane | 120 | 210 | 300 | 305 | 315 | 330 |
| 0.45% | N-butylaminomethane-diphosphonic acid | 19 | 21 | 23 | 26 | 31 | 43 |
| 0.45% | N-methylpyrrolidone-5,5-diphosphonic acid | 14 | 16 | 18 | 22 | 27 | 40 |
| 0.45% | 1-methyl-2-hydroxy-2-oxo-3-methylamino-3-phosphonyl-6-oxo-1,2-azaphosphacyclohexane | 10 | 11 | 14 | 18 | 22 | 32 |
| 0.45% | 2-phosphono-butane-1,2,4-tricarboxylic acid | 14 | 15 | 18 | 23 | 31 | 40 |
| 0.45% | ethylenediamine-tetra-(methylenephosphonic acid) | 115 | 120 | 124 | 127 | 130 | 136 |

In this series of measurements the best of the comparative substances only reached exactly half of the stabilizing action with three times the amount used, compared with the phosphonic acid according to the present invention.

EXAMPLE 3

In a series of experiments analogous to those of Example 1, samples of dibasic calcium phosphate dihydrates were prepared which were treated with the amounts of the respective inhibitors indicated in Table 3. The results of the hydrolysis measurements are seen in the following Table 3.

TABLE 3

| | Inhibitor | Time for x % Hydrolysis (Minutes) | | | | | |
|---|---|---|---|---|---|---|---|
| | | 10% | 20% | 40% | 60% | 80% | 100% |
| 0.75% | 2-hydroxy-2-oxo-3-amino-3-phosphonyl-7-oxo-1,2-azaphosphacycloheptane | 540 | 1250 | 1820 | 1830 | 1835 | 1845 |
| 0.75% | N-butylaminomethane-diphosphonic acid | 14 | 16 | 18 | 21 | 25 | 35 |
| 0.75% | N-methylpyrrolidone-5,5-diphosphonic acid | 11 | 12 | 14 | 18 | 24 | 40 |
| 0.75% | amino-tris-(methylene-phosphonic acid) | 15 | 17 | 20 | 24 | 28 | 35 |
| 0.75% | ethylenediamine-tetra-(methylenephosphonic acid) | 140 | 145 | 148 | 152 | 156 | 165 |

In this series of experiments the 2-hydroxy-2-oxo-3-amino-3-phosphonyl-7-oxo-1,2-azaphosphacycloheptane according to the present invention shows its complete superiority. Using the same concentration, a ten times stronger action is obtained compared with other hitherto used phosphonic acids.

EXAMPLE 4

A CaHPO$_4$.2H$_2$O cleaning material already stabilized by known means and commercially obtainable was treated according to the process described in Example 1 additionally with 0.75% of various phosphonic acids according to the present invention and the hydrolysis was measured. The additional stability to hydrolysis resulting therefrom was compared with a sample not additionally treated and with a sample which was treated with a phosphonic acid already known for this purpose. It shows that the compounds according to the present invention give a distinct additional inhibition, which is far superior to that of already known compounds. The values obtained by the measurements are given in the following Table 4.

TABLE 4

| Additional Inhibitor | | Time for 100% Hydrolysis (Minutes) |
|---|---|---|
| | Without addition | 140 |
| 0.75% | amino-tris-(methylenephosphonic acid) | 185 |
| 0.75% | 2-hydroxy-2-oxo-3-amino-3-phosphonyl-7-oxo-1,2-azaphosphacycloheptane | 1740 |
| 0.75% | 2-hydroxy-2-oxo-3-amino-3-phosphonyl-6-oxo-1,2-azaphosphacyclohexane | 1535 |

In the following examples formulations for tooth cleaning preparations are given which contain dibasic calcium phosphate dihydrate stabilized according to the present invention as a polishing material.

EXAMPLE 5

Composition of a toothpaste according to the present invention.

| | Parts by weight |
|---|---|
| Glycerine | 30.0 |
| Water | 18.0 |
| Sodium carboxymethylcellulose | 1.0 |
| Dibasic calcium phosphate dihydrate stabilized with 1% of 2-hydroxy-2-oxo-3-amino-3-phosphonyl-7-oxo-1,2-azaphosphacycloheptane | 36.0 |
| Insoluble sodium metaphosphate | 10.0 |
| Sodium lauryl sulfate | 1.0 |
| Pyrogenic silicic acid | 1.5 |
| Sodium monofluorophosphate | 0.5 |
| Essential oils | 1.5 |
| Saccharin sweetener | 0.5 |

Instead of Stabilizer C used in the above formulation for stabilizing the dibasic calcium phosphate dihydrate, Stabilizers A and B can be used in the same amounts with the same good results.

EXAMPLE 6

Composition of a tooth powder according to the present invention.

| | Parts by weight |
|---|---|
| Dibasic calcium phosphate dihydrate, stabilized with 1% of 2-hydroxy-2-oxo-3-amino-3-phosphonyl-7-oxo-1,2-azaphosphacycloheptane | 50.0 |
| Precipitated chalk | 30.0 |

| | Parts by weight |
|---|---|
| Finely divided silicic acid | 10.0 |
| Milk sugar | 4.0 |
| Precipitated magnesium carbonate | 4.0 |
| Titanium dioxide | 1.0 |
| Tannin | 1.0 |

Instead of the Stabilizer C used in the above formulation for the stabilization of the dibasic calcium phosphate dihydrate, Stabilizers A and B may be used in the same amount with the same good results.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A process for stabilizing dibasic calcium phosphate dihydrate against hydrolysis consisting essentially of suspending dibasic calcium phosphate dihydrate in an aqueous medium at a pH of from 5 to 10, containing from 0.01% to 5% by weight based on the content of said dibasic calcium phosphate dihydrate of a cyclic aminophosphonic compound selected from the group consisting of (A) compounds of the formula

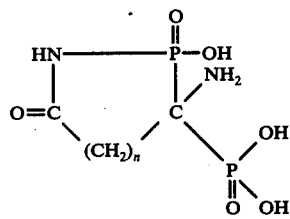

wherein $n$ is an integer from 1 to 3, and (B) water-soluble salts thereof, and separating said stabilized dibasic calcium phosphate dihydrate.

2. The process of claim 1 wherein said pH is between 6 and 8.

3. The process of claim 1 wherein the amount of said cyclic aminophosphonic acid compound is from 0.03 to 2% by weight based on the content of said dibasic calcium phosphate dihydrate.

4. The process of claim 1 wherein said water-soluble salts are selected from the group consisting of the alkali metal salts and ammonium salts.

5. A dibasic calcium phosphate dihydrate stabilized against hydrolysis by a cyclic amino-phosphonic acid produced by the process of suspending dibasic calcium phosphate dihydrate in an aqueous medium at a pH of from 5 to 10, containing from 0.01 to 5% by weight based on the content of said dibasic calcium phosphate dihydrate of a cyclic amino-phosphonic compound selected from the group consisting of (A) compound of the formula

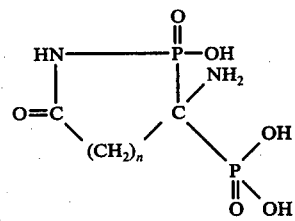

wherein $n$ is an integer from 1 to 3, and (B) water-soluble salts thereof, and separating said stabilized dibasic calcium phosphate dihydrate.

* * * * *